US006339716B1

(12) United States Patent
Sawada et al.

(10) Patent No.: US 6,339,716 B1
(45) Date of Patent: Jan. 15, 2002

(54) METHOD FOR DETERMINING VIABILITY OF A MYOCARDIAL SEGMENT

(75) Inventors: Stephen G. Sawada, Indianapolis, IN (US); John St. Cyr, Coon Rapids; Clarence A. Johnson, Wyoming, both of MN (US)

(73) Assignee: Bioenergy Inc., Ham Lake, MN (US)

( * ) Notice: Subject to any disclaimer, the term of this patent is extended or adjusted under 35 U.S.C. 154(b) by 0 days.

(21) Appl. No.: 09/405,462

(22) Filed: Sep. 24, 1999

(51) Int. Cl.$^7$ .............................. A61B 5/05; A61B 5/02; A61B 5/00; A61B 8/02; A61B 5/04

(52) U.S. Cl. ..................... 600/407; 600/425; 600/436; 600/365; 600/476; 600/479; 600/450; 600/449

(58) Field of Search ................................. 600/407, 425, 600/436, 365, 476, 479, 450, 449

(56) References Cited

U.S. PATENT DOCUMENTS

| | | | |
|---|---|---|---|
| 4,605,644 A | | 8/1986 | Foker ........................... 514/45 |
| 4,719,201 A | | 1/1988 | Foker ........................... 514/23 |
| 4,824,660 A | | 4/1989 | Angello et al. ............... 424/1.1 |
| 4,871,718 A | | 10/1989 | Carniglia ...................... 514/23 |
| 4,920,098 A | | 4/1990 | Cotter et al. ................... 514/2 |
| 4,968,719 A | | 11/1990 | Brevetti ....................... 514/556 |
| 5,114,723 A | | 5/1992 | Stray-Gunderson ........... 426/74 |
| 5,292,538 A | | 3/1994 | Paul et al. ..................... 426/74 |
| 5,391,550 A | | 2/1995 | Carniglia et al. ............. 514/23 |
| 5,477,857 A | * | 12/1995 | McAfee et al. ............. 600/431 |
| 5,707,971 A | | 1/1998 | Fahy ............................ 514/43 |
| 5,714,515 A | * | 2/1998 | Bunger ....................... 514/557 |
| 5,922,703 A | * | 7/1999 | Yu et al. ...................... 514/182 |
| 6,139,819 A | * | 10/2000 | Unger et al. ................ 424/952 |
| 6,159,942 A | * | 12/2000 | St. Cyr et al. ................ 514/23 |

FOREIGN PATENT DOCUMENTS

| | | | |
|---|---|---|---|
| DE | 4228215 | 3/1994 | .......... A61K/31/70 |
| EP | 0573466 | 12/1993 | .......... A61K/31/70 |
| EP | 0894439 | 2/1999 | ............ A23L/2/38 |
| WO | 92/15311 | 9/1992 | .......... A61K/31/70 |
| WO | 99/65476 | 12/1999 | .......... A61K/31/00 |

OTHER PUBLICATIONS

Angello, D.A. et al., "Recovery of Myocardial Function and Thallium 201 Redistribution Using Ribose", *Journal of Cardiac Imaging*, 3 (4), pp. 256–265. (Dec. 1989).

Batista, R., "Partial left ventriculectomy—the Batista procedure", *European Journal of Cardio–Thoracic Surgery*, 15 (Suppl. 1), pp. S12–S19, (Jan. 1999).

Bax, J.J., et al., "Accuracy of Currently Available Techniques for Prediction of Functional Recovery After Revascularization in Patients with Left Ventricular Dysfunction Due to Chronic Coronary Artery Disease: Comparison of Pooled Data", *Journal of the American College of Cardiology*, 30 (6), pp. 1451–1460, (Nov. 15, 1997).

Furnary, A.P., et al., "Multicenter Trial of Dynamic Cardiomyoplasty for Chronic Heart Failure", *Journal of the American College of Cardiology*, 28 (5), pp. 1175–1180, (Nov. 1, 1996).

Gross, M., et al., "Metabolism of D–Ribose Administered Continuously to Healthy Persons and to Patients with Myoadenylate Deaminase Deficiency", *Klin Wochenschr*, 67, pp. 1205–1213, (1989).

Jessup, M., "Optimizing Medical Management of the Patient with Severe Heart Failure Awaiting Cardiac Transplantation", *Cardiology—In Review*, 4 (5), pp. 286–291, (Sep. 1996).

Sawada, S.G., et al., "Echocardiographic Detection of Coronary Artery Disease During Dobutamine Infusion", *Circulation*, 83 (5), pp. 1605–1614, (May 1991).

Tullson, P.C. et al., "Adenine NucLEotide Syntheses in Exercising and Endurance–trained Skeletal Muscle", *The American Journal of Physiology*, 261 (2), pp. C342–C347, (1991).

Tullson, P.C., et al., "IMP Metabolism in Human Skeletal Muscle After Exhaustive Exercise", *The American Journal of Physiology*, pp. 146–152, (1995).

Zollner, N., et al., "Myoadenylate Deaminase Deficiency: Successful Symptomatic Therapy by High Dose Oral Administration of Ribose", *Klin Wochenschr*, 64, pp. 1281–1290, (1986).

Angello, D.A., et al.,"Effect of ribose on thallium–201 myocardial redistribution", *The Journal of Nuclear Medicine*, 29 (12), pp. 1943–1950, (Dec. 1990).

Hegewald, M.G., et al., "Ribose Infusion Accelerates Thallium Redistribution with Early Imaging Compared with Late 24–Hour Imaging Without Ribose", *JACC*, 18 (7), pp. 1671–1681, (Dec. 1991).

Ma, L., et al., "Nitroglycerin enhances the ability of dobutamine stress echocardiography to detect hibernating myocardium", *Circulation*, 96 (11), pp. 3992–4001, (Dec. 2, 1997).

(List continued on next page.)

*Primary Examiner*—Marvin M. Lateef
*Assistant Examiner*—Talaya James
(74) *Attorney, Agent, or Firm*—Schwegman, Lundberg, Woessner & Kluth, P.A.

(57) ABSTRACT

A method of determining the viability of a hibernating or stunned myocardial segment comprises the administration of ribose, a vasodilator and an inotropic agent. The preferred agent is dobutamine, which has both a vasodilation and an inotropic effect. The segments may be identified by myocardial imaging by any known means, such as echocardiography, Thallium-201 tracing or positron emission tomography. Ribose is preferably given one minute to three hours prior to administration of the vasodilator and inotropic agents.

10 Claims, No Drawings-

OTHER PUBLICATIONS

Nagueh, S.F., et al., "Identification of Hibernating Myocardium: comparative accuracy of myocardial contrast echocardiography, rest–redistribution thallium–201 tomography and dobutamine echocardiography", *JACC* 29 (5), pp. 985–993, (Apr. 1997).

Wagner, D.R., et al., "Effects of oral ribose on muscle metabolism during bicycle ergometer in AMPD–deficient patients", *Annals of Nutrition and Metabolism*, 35 (5), pp. 297–302, (1991).

* cited by examiner

METHOD FOR DETERMINING VIABILITY OF A MYOCARDIAL SEGMENT

BACKGROUND OF THE INVENTION

In patients with ischemic heart disease, regions of the heart may be poorly perfused, dysfunctional, but still viable. Myocardial ischemia limits blood flow and therefore the available supply of oxygen. This limited availability of oxygen affects oxidative metabolism, which ultimately negatively affects the production of adenosine triphosphate (ATP), essential for maintenance of contractility and cellular integrity. Varied states of ischemia exist. However, either transient or chronic ischemia may result in partial reduction of myocardial ATP with subsequent impairment of contractile function, but not cell death.

Various diagnostic methods have been developed to aid in determining whether areas of myocardium are "hibernating," "stunned," or are non-viable. Hibernating myocardium is generally considered to be myocardium that has modulated its function and therefore energy requirements in response to chronic poor perfusion. Stunned myocardium denotes an acute, transient episode of poor perfusion due to coronary vasospasm, coronary artery disease or other maladies. This determination of viable, though poorly functioning mycardium, versus non-viable myocardium is essential to first, identify and second, to predict eventual clinical outcome following a revascular intervention. One newly developed therapy where, the distinguishing of viable versus non-viable myocardium is crucial for an optimal outcome, is the partial left ventriculectomy or remodeling procedure of Batista (R. Batista, Eur. J. Cardiothoracic Surg., (1999) Suppl. 1, pp. 512. See particularly the discussion on pp. 539–43.)

End stage heart disease is often treated by transplantation of a healthy donor heart. Approximately 2500 patients were listed and waiting for heart transplant in the United States in 1996, with an additional 300 new listings each month. The availability of donor hearts is limited and typically, about 20% of those on the list die before a suitable heart is available. (Jessup, Mariell: Cardiol. Rev. (1996) 4:5, 286–191.) The usual criteria for selection to this waiting list covers a wide spectrum of patients, from those in extremely critical condition, close to death, to others who could be well sustained on aggressive drug therapy for a time period, with potential improvement in cardiac status, if a more accurate assessment of vitality were possible. Clearly, the recipient evaluation process would benefit from the application of objective, quantifiable criteria needed for estimating either success of transplant or the determinants of survival without transplant.

Many techniques have been developed to measure blood flow and cardiac function in the various segments of the heart. Bax et al. published a review of currently available techniques, which include positron emission tomography with fluorine-18 fluorodeoxyglucose, thallium (Tl)-201 stress- redistribution-reinjection, Tl-201 rest-distribution, single photon emission tomography with technetium-99 m and low dose dobutamine echocardiography. (Bax et al J. Am. Coll. Cardiol. (1997) 30:1451–1460.)

Positron emission tomography (PET) scans have been considered to be the gold standard as a tool of diagnostic cardiology, however, newer computer-based techniques for acquisition and display of echocardiograms have generated increasing interest in the method for assessing the condition of the myocardium (Sawada et al. (1991) Circulation, 83: 1605–1614.) Measurement of ventricular wall thickness, segmental wall movement, ejection fraction and volume have been correlated with myocardial function. During echocardiography, a radar signal is sent through an esophageal or transthoracic probe, into the chest, and picked up by a monitor. A dobutamine infusion uncovers areas of reduced perfusion that were not apparent prior to using dobutamine. Studies have shown that segmental wall motion abnormalities can correlate with the distribution of at least one significantly diseased vessel in 93% of the patients with multivessel or main vessel disease.

The need remains for an improved method for distinguishing viable from non-viable myocardium as a diagnostic tool and for decision-making in subsequent therapy.

BRIEF SUMMARY OF THE INVENTION

It has been investigated and is here disclosed that the beneficial effects of D-ribose on ATP levels, in the presence of a vasodilator and/or inotropic agent, improves the identification of viable versus non-viable myocardium in patients with cardiovascular disease. The effect of D-Ribose on wall motion seen on echocardiography examination was studied in various populations suspected of having stunned or hibernating myocardium.

This invention provides an improved method to diagnose viability of myocardial segments which have the potential for functional recovery after revascularization. This invention further provides D-Ribose alone or preferably in combination with vasodilators and/or inotropic agents to increase the sensitivity of detection of viable, stunned or hibernating tissue.

DETAILED DESCRIPTION OF THE INVENTION

Myocardial hibernation and stunning define conditions in which tissue viability may be present but is hindered in the presence of reduced regional or global blood flow. The phenomenon of hibernating and stunned myocardium has been the subject of increasing interest with recognition that function may improve in these regions after restoration of adequate blood supply or treatment with newly available therapies such as the Batista procedure, in which the diastolic volume of the ventricle is surgically reduced by removal of non-viable or poorly viable tissue. The resulting ejection efficiency of the ventricle is improved with the patient usually experiencing a clinical benefit.

Among the techniques used to distinguish non-viable from viable myocardium, echocardiography is commonly used because of its direct measurement of contractile function, which is thought to be a better predictive indicium than blood-flow tracing with radionuclides. However, the sensitivity of this method, as with other methods such as thallium imaging and PET scan, may be limited in the presence of severe coronary artery disease (CAD). It has been previously found that the use of low dose dobutamine enhances the diagnosis of viable myocardium (Sawada et al, 1991). It has also been previously found that D-Ribose improves thallium imaging. (Angello et al, (1989) Am. J. Ar. Imag. 3:256–265.) It has now been discovered that the diagnosis is further enhanced by the combination of a vasodilator, inotropic agent and D-Ribose, leading to a more optimal clinical outcome.

Coronary artery bypass grafting (CABG) has become a routine procedure. During this procedure, blood flow is restored to regions of the heart served by stenotic coronary arteries. Identification of those areas that are hibernating or stunned rather than non-viable aids the surgeon in revascularizing those regions that are most capable of being revived and improved with reperfusion.

Once viability has been determined, various methods of revascularization may be considered by the medical personnel and offered to the patient. Ischemia may be viewed in the disease state as either acute or chronic, and decisions made according to the following Table:

TABLE I

Choice of Therapy for Coronary Artery Disease

| ACUTE ISCHEMIA (myocardial infarction or coronary arteriospasm) | CHRONIC ISCHEMIA (coronary artery occlusion) |
|---|---|
| CABG coronary balloon angioplasty coronary artery atherectomy | CABG coronary balloon angioplasty coronary artery atherectomy transmyocardial revascularization heart transplant |

Each treatment carries its own risks and benefits. For example, angioplasty has a lower rate of long-term success than CABG due to the tendency of the vessel to reocclude ("restenosis"), but because it is a simpler procedure with lower risks, it will be often indicated as a first course of action, when the patient has an amenable lesion. However, not all patients carry the same preoperative risk for each procedure. If the heart contains large areas of non-viable tissue with severely decreased myocardial performance, a heart transplant rather than CABG may be the patient's only alternative.

The references identified in the specification are incorporated herein by reference to the extent that they supplement, explain, provide background for, or teach the methodology, techniques and/or compositions employed herein.

The following examples are included to demonstrate preferred embodiments of the invention. In each example, D-Ribose is disclosed as the preferred embodiment. However, it is known in the art that certain pentoses such as xylitol and ribulose are readily converted to D-Ribose in vivo. Therefore, the term "D-Ribose" is intended to include such precursors of D-Ribose. D-Ribose is readily absorbed from the intestinal mucosal or from the peritoneum, and can therefore be administered orally, by intravenous infusion or by peritoneal infusion. Likewise, the examples use dobutamine as a vasodilator/inotropic agent. Dobutamnine in the agent of choice because it has a dual effect on the myocardium, acting both to dilate the coronary arteries and as an inotrop to increase the contractility of the myocardium. Dobutamine can readily be replaced by similar compounds such as arbutamine or isoproterenol. However, those of skill in the art can readily appreciate that a combination of vasodilators and inotrops will produce an equivalent effect. Such vasodilators that can be used are listed as Group I: dobutamine, arbutamine, nitroglycerine, nitrates, nitrites, papaverine, isoproterenol, nylidrin, isoxsuprine, L-arginine, nitroprusside, adenosine, xanthines, ethyl alcohol, dipyramide, hydralazine, minoxidil, diazoxide and analogs of the foregoing. In addition, endogenous vasodilators such as nitric oxide and prostaglandins can be induced. Inotropic agents are listed as Group II: dobutamine, arbutamine, dopamine, amrinone, milrinone, and analogs of the foregoing. This invention therefore includes the use of D-Ribose or its equivalents plus dobutamine or its equivalents, including those equivalents formed by a combination of an agent chosen from each of Group I and Group II.

It should be appreciated by those skilled in the art that the techniques and dosages disclosed in the examples that follow represent techniques and dosages discovered by the inventors to function well in the practice of this invention, and thus can be considered to constitute preferred modes for its practice. However, those skilled in the art should, in light of the present disclosure, appreciate that many changes can be made in the specific embodiments that are disclosed and still obtain a like or similar result without departing from the concept and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 1

Echocardiography

A single-center, randomized, double-blind placebo-controlled clinical trial was carried out to evaluate the safety and efficacy of D-Ribose on myocardial wall motion during echocardiographic examination in patients suspected of having stunned or hibernating myocardium.

Patients included:

ages 18 or older, male or female stable resting wall motion abnormalities noted on baseline echocardiography, defined as at least two segments with abnormal function.

at least five days from a major cardiac event such as myocardial infarction or unstable angina no known allergies or contraindications to D-Ribose or dobutamine stable medical regimen of vasoactive medications known coronary artery disease (CAD) discovered by cardiac catheterization, myocardial infarction or positive stress test OR patients with high index of suspicion for CAD provided they have a resting wall abnormality on ECHO for females of child-bearing potential, a negative pregnancy test signed informed consent approved by an Institutional Review Board Patients excluded:

diabetes mellitus requiring insulin or an oral hypoglycemic agent inability to sign consent form history of non-ischemic cardiomyopathy clinically significant liver or renal disease in the judgment of the investigator advanced valvular heart disease in the judgment of the investigator Patients were randomized into placebo and ribose groups according to a computer generated randomization schedule. The identity of the contents was blinded to the investigator. Patients were identified by initials. The selected study population was comprised of 25 patients (22 men and 3 women) with a mean age of 57+/−11 years. All had reduced left ventricular systolic function (mean ejection fraction 30+/− 8%, range 18 to 48%). Twenty-two patients (88%) had prior myocardial infarction and only one subject was evaluated after recent (<4 weeks) infarction. Nineteen patients (76%) had stable angina pectoris and 21 (84%) were receiving one or more medications to treat ischemia (nitrates (21), betaantagonists; (9), calcium channel antagonists (9). Coronary artery disease (≧50% diameter stenosis) was documented by angiography in 22 patients. Of the 21 who had recent studies, 12 had three-vessel, 8 had two-vessel and one had single vessel disease. Subjects were admitted to the hospital on the morning of study day 1 after an 8 hour fast. After a limited physical examination, a baseline (AM) echocardiogram was obtained. Following the imaging study, continuous monitoring of the heart rhythm was initiated.

After completion of the baseline echocardiography, intravenous infusion of test article (D-Ribose or placebo) at a set infusion, along with an infusion of 5% glucose in water (D5W) at 100 ml/hour as a maintenance fluid was initiated. D-Ribose, 10% in water at 180 mg/kg/hour, or placebo D5W at 1.8 mg/kg/hour, were given as sterile, pyrogen-free solutions. After the test article had been administered for one, two, three or four hours, a resting echocardiogram was obtained. At completion of this rest period, dobutamine was infused. Dobutamine hydrochloride (Dobutrex® solution, Eli Lilly, Indianapolis ) was mixed in D5W (5% dextrose in water), giving a concentration of 1.0 mg/ml. During echocardiography, dobutamine was administered at an initial dose of 5 μg/kg/minute for three minutes. The dose of dobutamine was then increased to 10 μg/kg/min and infused for three minutes. Echocardiograms were obtained at the low dose stages and at peak stage. Every three minutes the concentration of dobutamine was increased by 10 μg/kg/minute increments until the standard endpoint was reached. The standard endpoint was set to be a greater than 2 mm ST-segment depression on ECG; significant side effects or arrhythmias; achievement of 85% of the age-predicted maximal heart rate; a systolic blood pressure >250 mm Hg, a significant fall in systolic blood pressure or a maximal dose of 50 μg/kg/minute.

Post-infusion images were recorded approximately eight minutes after discontinuation of dobutamine. Upon completion of imaging, the test article infusion was terminated. Subjects were observed overnight and on Day 2 were crossed over to the alternate test article. Study protocols on Day 2 were identical to those of Day 1.

EXAMPLE 2

Echocardiographic Analysis

Baseline (AM) and PM two-dimensional echocardiograms and any post-revascularization studies were performed using an Advanced Technology Laboratories UM9 HDI (Bothell, Wash.) with a 3.0 MHZ phased array transducer and a Hewlett Packard Sonos 1500 (Andover, Mass.) with a 2.5 MHZ phased array transducer. Parasternal long and short-axis and apical two and four-chamber images were recorded on 0.5 inch videotape and digitally stored on floppy discs using a Nova MicroSonics DCR or Colorvue system (Mahwah, N.J.). End-diastolic and systolic images were acquired on line at 67 msec intervals.

The Day 1 and Day 2 AM and PM echocardiograms for each subject were transferred from floppy disk to a customized image network where each subject's images were archived only by hospital number. The images were retrieved from the network and analyzed using the Indiana University Off-line Revue System. Once retrieved, the images were rearranged in computer memory to display AM and PM images side by side for each echocardiogram view. Two blinded investigators rendered a consensus interpretation of regional wall motion in 16 left ventricular segments. Wall motion was graded as: (1) normal; (2) mildly hypokinetic with <5 mm inward systolic motion; (2.5) severely hypokinetic with minimal inward systolic motion and wall thickening; (3) akinetic with an absence of inward motion and wall thickening; (4) dyskinetic with paradoxical outward motion. A global wall motion score was derived for each echocardiogram (sum of individual segment scores per number of segments scored).

The Day 1 and Day 2 dobutamine echocardiograms comprised of resting, 5, 10 μg/kg/minute, and peak dose images were stored and reviewed using the procedures and equipment previously described for the AM and PM images, except that side by side comparison was not performed. Using the previously described scoring system, regional wall motion was graded by consensus by two blinded investigators. Hyperdynamic wall motion during dobutamine infusion was scored as one normal wall motion. A one grade improvement of wall motion during dobutamine infusion was considered significant. Global wall motion scores were derived for each stage of the dobutamine echocardiogram.

During low-dose dobutamine infusion (5μ/kg/minute), wall motion improved in more segments on D-Ribose than placebo (65 segments v. 48 segments ). Eleven patients subsequently underwent CABG after completion of Study Day 2. At least one echocardiogram was obtained postoperatively in each of these subjects. Regional wall motion was compared between the follow-up echocardiogram and the Day 1 AM study by two blinded investigators. A single, blinded investigator made determinations of ejection fraction on the AM, PM, dobutamine and any post-revascularization echocardiograms using the four-chamber view and the Simpson's method.

Table II summarizes the sensitivity, specificity and accuracy of improvemnent of ejection fraction during dobutamine plus D-Ribose versus dobutamine plus placebo for prediction of improvement in ejection fraction after CABG. Significant improvement is defined as Post-bypass ejection fraction increase ≧10% for analysis 2.

TABLE II

Improvement of Ejection Fraction Following CABG

| | Analysis 1: EF Increase ≧ 5% | | Analysis 2: EF Increase ≧ 10% | |
| --- | --- | --- | --- | --- |
| | Ribose | Placebo | Ribose | Placebo |
| Sensitivity | 89% (8/9) | 56% (5/9) | 57% (4/7) | 29% (2/7) |
| Specificity | 50 (1/2) | 0 (0/2) | 100 (4/4) | 25 (1/4) |
| Accuracy | 82 (9/11) | 45 (5/11) | 73 (8/11) | 27 (3/11) |

The accuracy of dobutamine plus D-Ribose in identifying patients with an increase in ejection fraction (EF) following surgery of greater than or equal to 10% is shown in Table II. In the 11 patients who had coronary artery bypass grafting, segments that showed improvement in wall motion after bypass were considered to have hibernating myocardium. EF measured after revascularization showed that nine subjects had an increase in EF of at least five percent. Eight of the nine, or 89% had been diagnosed using ribose. Seven of these subjects showed an increase of ≧ ten percent. The accuracy of a greater than ten percent improvement in EF after bypass was 73% for dobutamine plus D-Ribose compared to 27% for dobutamine plus placebo. Therefore, the addition of D-Ribose to dobutamine for identification of hibernating or stunned myocardium confers an advantage over the dobutamine alone.

All of the compositions and methods disclosed and claimed herein can be made and executed without undue experimentation in light of the present disclosure. While the compositions and methods of this invention have been described in terms of preferred embodiments, it will be apparent to those skilled in the art that variations may be applied to the compositions and methods described herein without departing from the concept and scope of the invention. More specifically, it will be apparent that certain agents that are both chemically and physiologically related may be substituted for the agents described herein while the same of similar results would be achieved. All such similar substitutes and modifications apparent to those skilled in the art are deemed to be within the scope and concept of the invention as defined by the appended claims.

We claim:

1. A method of determining the viability of a segment of hibernating or stunned myocardium comprising administering effective amounts of ribose, a vasodilator and an inotropic agent to the myocardium or performing myocardial imaging to detect myocardial function, thereby providing an indication of the viability of the myocardial segment.

2. The method of claim 1 wherein the vasodilator is selected from the group consisting essentially of dobutamine, arbutamine, nitroglycerine, nitrate, nitrite, papaverine, isoproterenol, nylidrin, isoxsuprine, L-arginine, nitroprusside, adenosine, xanthine, ethyl alcohol, dipyramide, hydralazine, minoxidil, and diazoxide and the inotropic agent is selected from the group consisting essentially of dobutamine, arbutamine, dopamine, amrinone and milrinone.

3. The method of claim 1 wherein the vasodilator and inotropic agent is dobutamine.

4. The method of claim 1 wherein the myocardial imaging is performed by echocardiography and the myocardial function is wall motion.

5. The method of claim 1 wherein the myocardial imaging is performed by positron emission tomography and the myocardial function is blood flow.

6. The method of claim 1 wherein the myocardial imaging is performed by Thallium-201 imaging and the myocardial function is blood flow.

7. The method of claim 1 wherein ribose is administered prior to imaging.

8. A method of determining the viability of a segment of hibernating or stunned myocardium comprising administering effective amounts of ribose and dobutamine to the myocardium and performing myocardial imaging to detect myocardial function, thereby providing an indication of the viability of the myocardial segment.

9. The method of claim 8 wherein the ribose is administered prior to myocardial imaging.

10. The method of claim 8 wherein the myocardial imaging is performed by echocardiography and the myocardial function is wall motion.

\* \* \* \* \*

UNITED STATES PATENT AND TRADEMARK OFFICE
CERTIFICATE OF CORRECTION

PATENT NO. : 6,339,716
DATED : January 15, 2002
INVENTOR(S) : Sawada et al.

It is certified that error appears in the above-identified patent and that said Letters Patent is hereby corrected as shown below:

<u>Column 7,</u>
Line 17, delete "or" and insert -- and --, therefor.

Signed and Sealed this

Twenty-first Day of May, 2002

*Attest:*

*Attesting Officer*

JAMES E. ROGAN
*Director of the United States Patent and Trademark Office*